(12) United States Patent
Desi Reddy et al.

(10) Patent No.: US 9,676,722 B2
(45) Date of Patent: Jun. 13, 2017

(54) INDUSTRIAL PROCESS FOR MAKING AN IVACAFTOR AND ITS INTERMEDIATES

(71) Applicant: Optimus Drugs Private Limited, Hyderabad (IN)

(72) Inventors: Srinivas Reddy Desi Reddy, Hyderabad (IN); Dnyandev Ragho Rane, Hyderabad (IN); Venkata Srinivasa Rao Velivela, Hyderabad (IN)

(73) Assignee: Optimus Drugs Private Limited, Hyderabad (IN)

( * ) Notice: Subject to any disclaimer, the term of this patent is extended or adjusted under 35 U.S.C. 154(b) by 0 days.

(21) Appl. No.: 15/246,246

(22) Filed: Aug. 24, 2016

(65) Prior Publication Data

US 2017/0096397 A1 Apr. 6, 2017

(30) Foreign Application Priority Data

Oct. 6, 2015 (IN) .......................... 5333/CHE/2015

(51) Int. Cl.
*C07D 215/233* (2006.01)
*C07D 215/56* (2006.01)
*C07C 213/02* (2006.01)

(52) U.S. Cl.
CPC .......... *C07D 215/56* (2013.01); *C07C 213/02* (2013.01)

(58) Field of Classification Search
CPC ................................................... C07D 215/233
USPC ........................................................ 546/156
See application file for complete search history.

(56) References Cited

U.S. PATENT DOCUMENTS 7,495,103 B2 2/2009 Hadida-Ruah et al.
8,476,442 B2 7/2013 DeMattei et al.

FOREIGN PATENT DOCUMENTS

EP 2489659 A1 8/2012

OTHER PUBLICATIONS

Eaton et al., Phosphorus pentoxide-methanesulfonic acid. Convenient alternative to polyphosphoric acid, J.. Org. Chem., 1973, 38(23):4071-4073.

*Primary Examiner* — Patricia L Morris
(74) *Attorney, Agent, or Firm* — Bret E. Field; Bozicevic, Field & Francis LLP

(57) ABSTRACT

The present invention relates to an improved process for the preparation of Ivacaftor intermediates. The present invention is also provides industrial applicable, commercially and eco-friendly viable process for the preparation of Ivacaftor.

19 Claims, No Drawings

INDUSTRIAL PROCESS FOR MAKING AN IVACAFTOR AND ITS INTERMEDIATES

FIELD OF THE INVENTION

The present invention relates to an improved process for the preparation of Ivacaftor intermediates. The present invention also provides industrial applicable, commercially and eco-friendly viable processes for the preparation of Ivacaftor

BACKGROUND OF THE INVENTION

"Ivacaftor" (INN, trade name Kalydeco) is being developed by Vertex pharmaceuticals for patients with a certain mutation of cystic fibrosis and it is classified as a cystic fibrosis transmembrane conductance regulator (CFTR) potentiator. Ivacaftor is chemically known N-(2,4-di-tert-butyl-5-hydroxyphenyl)-1,4-dihydro-4oxoquinoline-3-carboxamide, and has the structure of Formula (I).

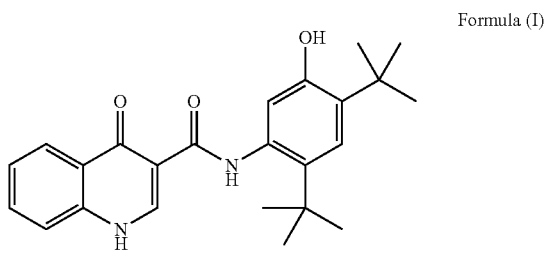 [SMILES: CC(C)(C)c1cc(C(C)(C)C)c(NC(=O)c2c[nH]c3ccccc3c2=O)cc1O]

Formula (I)

Ivacaftor was first disclosed in U.S. Pat. No. 7,495,103 and its process of preparation is disclosed as including reacting 4-Oxo-1,4-dihydro-quinoline-3-carboxylic acid of formula (II) with 2, 4 ditertiary butyl-5-nitro-phenol of formula (III) in presence of O-Benzotriazole-N,N,N',N'-tetramethyl-uronium-hexafluoro-phosphate (HBTU) and triethyl amine to obtain the compound of formula (I). The above synthetic process is illustrated as per the following Scheme-I

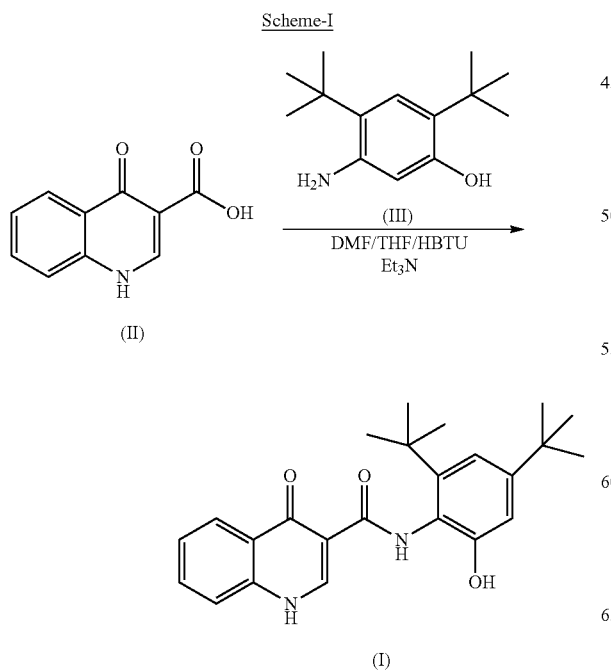

Scheme-I

The process for the preparation of intermediate of formula (II) as per U.S. Pat. No. 7,495,103 is illustrated as per the following Scheme-II

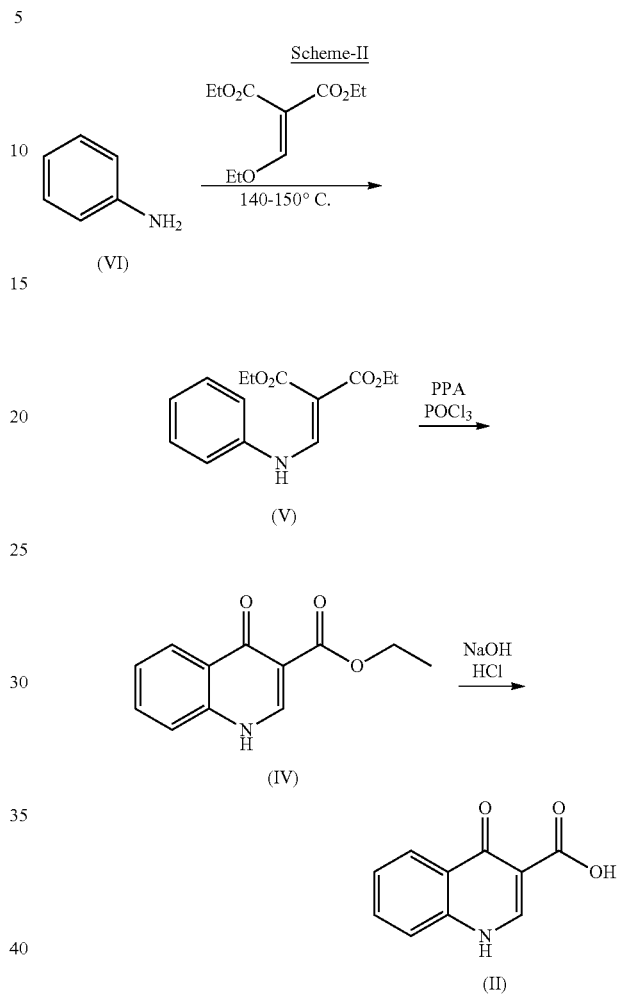

Scheme-II

The process for the preparation of intermediate of formula (III) as per U.S. Pat. No. 7,495,103 is illustrated as per the following Scheme-III

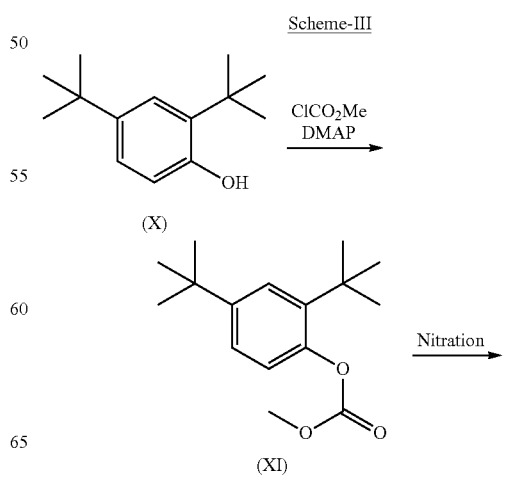

Scheme-III

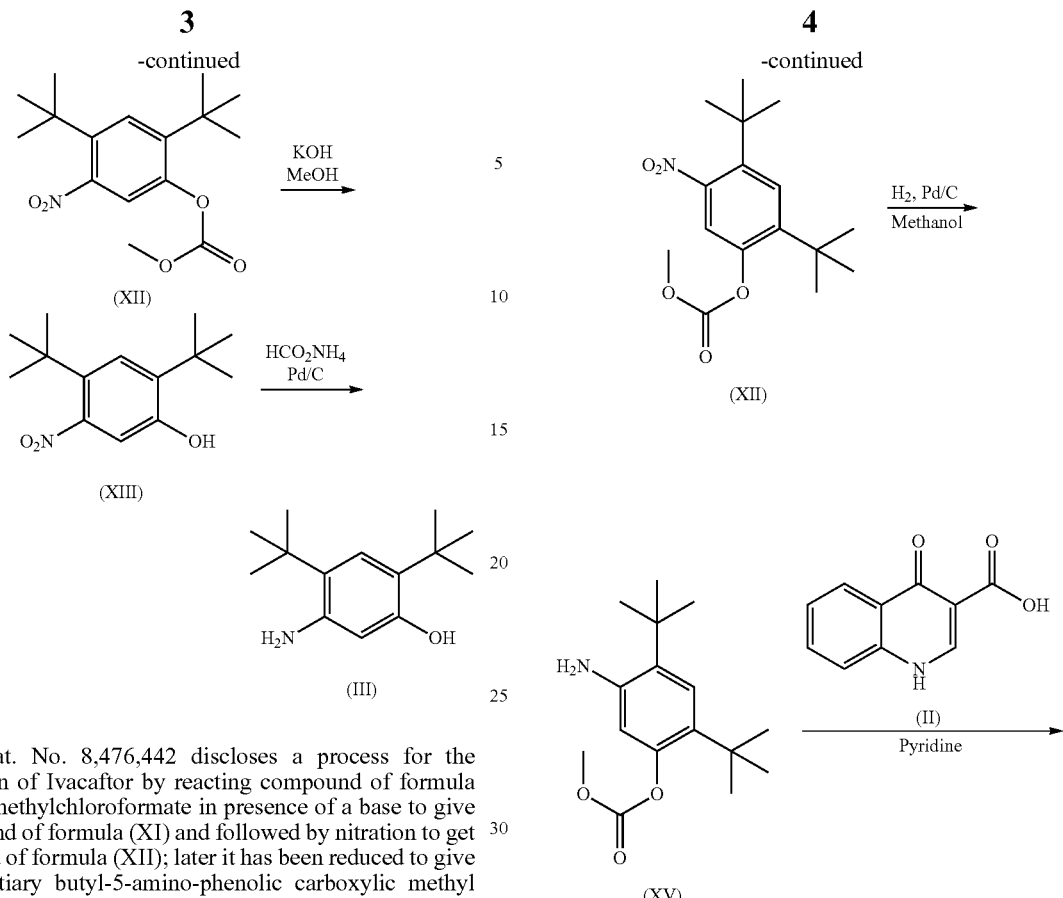

U.S. Pat. No. 8,476,442 discloses a process for the preparation of Ivacaftor by reacting compound of formula (X) with methylchloroformate in presence of a base to give a compound of formula (XI) and followed by nitration to get compound of formula (XII); later it has been reduced to give 2, 4 ditertiary butyl-5-amino-phenolic carboxylic methyl ester of formula (XV). 4-Oxo-1,4-dihydro-quinoline-3-carboxylic acid of formula (II) is condensed with a compound of formula (XV) to give a compound of formula (IX); further it is treated with sodium methoxide to give a crude Ivacaftor and it is recrystallized with isopropyl alcohol to give a pure compound of formula (I).

The above synthetic process of U.S. Pat. No. 8,476,442 is illustrated as per the following Scheme-IV

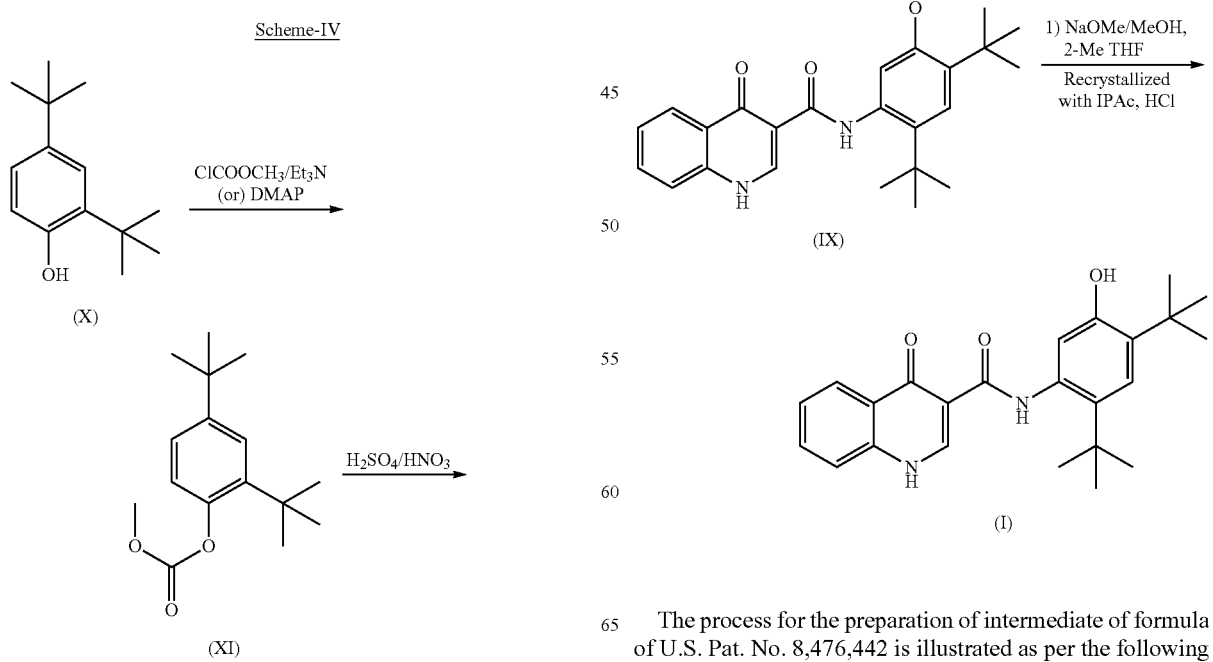

The process for the preparation of intermediate of formula of U.S. Pat. No. 8,476,442 is illustrated as per the following Scheme-V

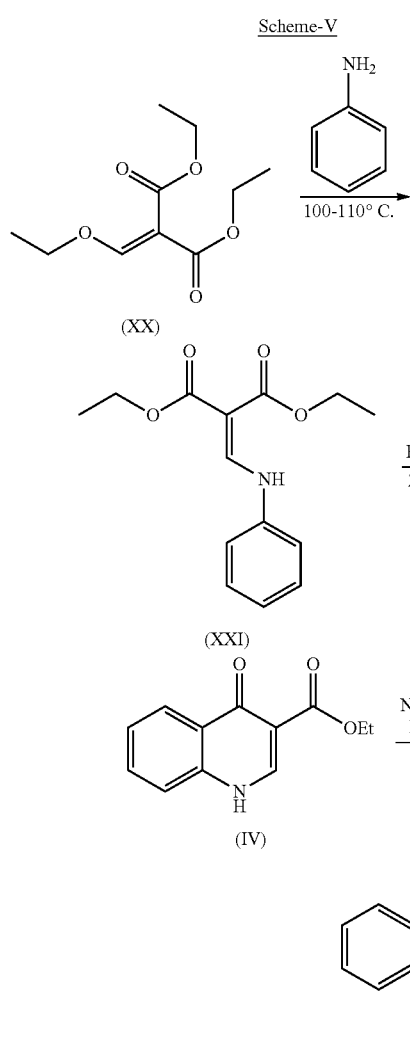

The complexity of the known prior art processes for the preparation of the Ivacaftor and its intermediates of formulas (II) and (III) are:
a) Expensive as isomeric separation of intermediate (III) requires column chromatography which is not applicable on an industrial scale;
b) Polyphosphoric acid and POCl₃ are used for cyclization of 4-hydroxyquinoline 3-carboxylic acid ethyl ester;
c) Both these reagents Polyphosphoric acid and POCl₃ are toxic and very difficult to handle at plant scale;
d) Polyphosphoric acid and POCl₃ are used in large quantities for the reaction, and subsequently large quantity of base is required for their neutralization; and
e) Large quantities of effluents are generated.

There is consequently a need for an alternative method for the preparation of Ivacaftor and its intermediates which does not involves the problems described above. Such methods should be more industrially scalable, economic and should employ reagents that are cheaper, easier to handle and allow only desired compounds to be obtained with a high purity yields.

SUMMARY

One aspect of the present invention is to provide an improved process for the preparation of compound of formula (II) comprising the steps of:

a) reacting aniline with diethyl-2-(ethoxymethylene) malonate;
b) treating the product of step a) with Eaton's reagent and heated to 80-90° C.;
c) cooling the product of step b) and neutralizing with an alkali carbonate;
d) hydrolyzing the product of step c) with an inorganic base; and
e) isolating the intermediate of formula (II).

The above synthetic process is illustrated as per the following Scheme-VI

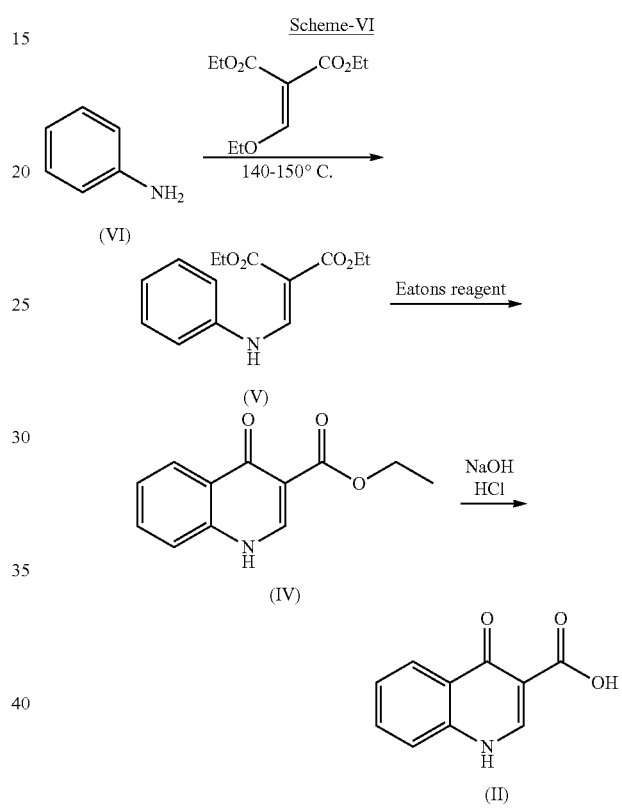

Another aspect of the present invention is to provide an improved process for the preparation compound of formula (III) comprising the steps of;
a) reacting the 2,5 di-tertiary butyl phenol with alkyl chloroformate in presence of a base;
b) nitrating the product of step a) to get a mixture of 2, 4 di-tert-butyl-5-nitro phenyl carboxylic alkyl ester and 2, 4 di-tert-butyl-6-nitro phenyl carboxylic alkyl ester,
c) separating the 2, 4 di-tert-butyl-5-nitro phenyl carboxylic alkyl ester by crystallization with an aliphatic solvent;
d) hydrolyzing the product of step c);
e) reducing the product of step d) in presence of Raney/nickel; and
f) isolating the compound of formula (III).

In another aspect of the present invention is to provide an improved process for the preparation compound of formula (III) comprising the steps of:
a) reacting the 2,5 di-tertiary butyl phenol with alkyl chloroformate in presence of a base;
b) nitrating the product of step a);

c) hydrolyzing the product of step b) to get a mixture of 2, 4 di-tert-butyl-5-nitro phenol and 2, 4 di-tert-butyl-6-nitro phenol;
d) separating the 2, 4 di-tert-butyl-5-nitro phenol by crystallization with an aliphatic solvent;
e) reducing the product of step d) in presence of Raney/nickel; and
f) isolating the compound of formula (III).

The above two aspects of the present invention is illustrated as per the following Scheme-VII

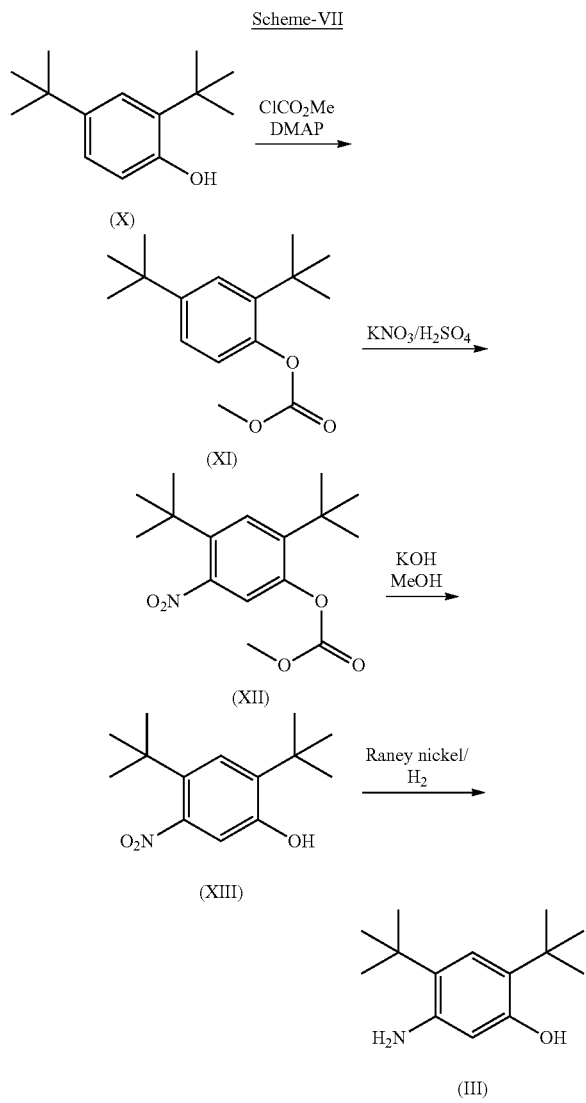

DETAILED DESCRIPTION

The present invention relates to an improved process for the preparation of Ivacaftor intermediates. The present invention also relates to a process for the preparation of Ivacaftor.

Before the present methods are described, it is to be understood that this invention is not limited to particular method described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the enzyme" includes reference to one or more enzymes and equivalents thereof.

The publications discussed herein are provided solely for their disclosure prior to the filing date of the present disclosure. Nothing herein is to be construed as an admission that the present invention is not entitled to antedate such publication by virtue of prior invention. Further, the dates of publication provided may be different from the actual publication dates which may need to be independently confirmed.

One embodiment of the present invention is to provide an improved process for the preparation of compound of formula (II) comprising the steps of:
a) reacting aniline with diethyl-2-(ethoxymethylene) malonate;
b) treating the product of step a) with Eaton's reagent and heating to 80-90° C.;
c) cooling the product of step b) and neutralizing with an alkali carbonate;
d) hydrolyzing the product of step c) with an inorganic base; and
e) isolating the intermediate of formula (I).

According to the embodiment of the present invention, a process of preparing compound of formula (II) is provided that comprises reacting aniline with diethyl-2-(ethoxymethylene) malonate in the absence of a solvent at 130-160° for 2-5 hrs; such as at 140-150° C. for 2-3 hrs, to obtain a compound of formula (V), which is further treated with Eaton's reagent to get a cyclized compound of formula (IV). The compound of formula (IV) is hydrolyzed in presence of a inorganic base to give a 4-Oxo-1,4-dihydro-quinoline-3-carboxylic acid of formula (II).

According to the embodiment, the Eaton's reagent is used for cyclizing the compound of formula (V) to get a compound of formula (IV) and its best to control the side chain reactions, which happen in prior art processes. Aforesaid prior art $POCl_3$ reagent is used in large quantities for cyclization; excess of this reagent is required a large amount of sodium carbonate is employed for quenching which leads to impurities, which are difficult to remove in further purification steps. Moreover, Eaton's reagent is cheaper, and more commercially and economically available.

According to the embodiment, the alkali carbonate in reaction step c) is selected from sodium bicarbonate, potassium carbonate, sodium carbonate and calcium carbonate.

According to the embodiment, the inorganic base in reaction step e) is selected from sodium hydroxide, calcium hydroxide and potassium hydroxide.

Another embodiment of the present invention is to provide an improved process for the preparation compound of formula (III) comprising the steps of:
  a) reacting the 2,5 di-tertiary butyl phenol with alkyl chloroformate in presence of a organic base:
  b) nitrating the product of step a) to get a mixture of 2, 4 di-tert-butyl-5-nitro phenyl carboxylic alkyl ester and 2, 4 di-tert-butyl-6-nitro phenyl carboxylic alkyl ester:
  c) separating the 2, 4 di-tert-butyl-5-nitro phenyl carboxylic alkyl ester by crystallization with aliphatic solvent:
  d) hydrolyzing the product of step c):
  e) reducing the product of step d) in presence of Raney/nickel: and
  f) isolating the compound of formula (III).

According to this embodiment of the present invention, a process of preparing a compound of formula (III) is provided, where the process comprises reacting 2,5 di-tertiary butyl phenol with alkyl chloroformate in presence of an organic base and an a solvent to obtain a 2, 4 di-tert-butylphenyl carboxylic alkyl ester which is then treated with potassium nitrate in presence of sulphuric acid to obtain a mixture of 4 di-tert-butyl-5-nitro phenyl carboxylic alkyl ester and 2, 4 di-tert-butyl-6-nitro phenyl carboxylic alkyl ester compound of formula (XII).

The mixture of formula (XII) is crystallized with an aliphatic solvent to separate 2, 4 di-tert-butyl-5-nitro phenyl carboxylic alkyl ester; which is further hydrolyzed in presence of an inorganic base to get a compound of formula (XIII) The compound of formula (XIII) is then reduced in presence of Raney nickel and a solvent to obtain a 2, 4 ditertiary butyl-5-amino-phenol of formula (III).

In yet another embodiment of the present invention, an improved process for the preparation compound of formula (III) is provided that comprises the steps of:
  a) reacting the 2,5 di-tertiary butyl phenol with alkyl chloroformate in presence of a organic base:
  b) nitrating the product of step a):
  c) hydrolyzing the product of step b) to get a mixture of 2, 4 di-tert-butyl-5-nitro phenol and 2, 4 di-tert-butyl-6-nitro phenol:
  d) separating the 2, 4 di-tert-butyl-5-nitro phenol by crystallization with aliphatic solvent:
  e) reducing the product of step d) in presence of Raney/nickel: and
  f) isolating the compound of formula (III).

According to the embodiment of the present invention, a process of preparing a compound of formula (Iii) is provided that comprises reacting 2,5 di-tertiary butyl phenol with alkyl chloroformate in presence of an organic base and a solvent to obtain a 2, 4 di-tert-butylphenyl carboxylic alkyl ester which is treated with potassium nitrate in presence of sulphuric acid to obtain a mixture of 4 di-tert-butyl-5-nitro phenyl carboxylic alkyl ester and 2, 4 di-tert-butyl-6-nitro phenyl carboxylic alkyl ester compound of formula (XII).

The compound of formula (XII) is hydrolyzed in presence of inorganic base to give a mixture of 2, 4 di-tert-butyl-5-nitro phenol and 2, 4 di-tert-butyl-6-nitro phenol; further it has been crystallized with aliphatic solvent to separate 2, 4 di-tert-butyl-5-nitro phenol. The compound of formula (XIII) is reduced in presence of Raney nickel and an solvent to give a 2, 4 ditertiary butyl-5-amino-phenol of formula (III).

According to the embodiments, the alkyl chloroformate is selected from ethyl chloroformate, methyl chloroformate (or) isopropyl chloroformate.

According to the embodiments, the nitrating agent is selected from $KNO_3/H_2SO_4$, $NaNO_3/H_2SO_4$ (or) $HNO_3/H_2SO_4$ According to the embodiments, the hydrolysis may take place in the presence of a base, which is selected from sodium hydroxide, calcium hydroxide and potassium hydroxide. The organic base is in some instances, selected from triethylamine, Dimethylaminopyridine (or) pyridine.

According to embodiments of the present invention, the solvent is selected from dichloromethane, ethylenedichloroethane, chloroform, methanol, ethanol (or) isopropanol.

According to embodiments of present invention, the aliphatic solvent is selected from n-hexane, cyclohexane, isobutyl ether, Tetrahydrofuran (or) methyl tertiary butyl ether; and the aromatic solvent is selected from toluene, mesitylene (or) xylene.

According to embodiments of the present invention, the reduction of nitro compound in presence of Raney nickel/$H_2$ yields a light pink color product and after purification with a aromatic solvent provides a high purity compound of formula (III). When compared to aforesaid prior art process, the prior art process yields a dark brown color with more impurities. Moreover, the Raney nickel is a cheaper reducing agent, and more commercially and economically as compared to Palladium carbon/ammonium formate.

According to embodiments of the present invention, the intermediates of formula (II) and (III) have HPLC purity of not less than 99%.

According to embodiments of the present invention, there is no need for column purification to isolate the intermediates of formula (II) and (III).

According to embodiments of the present invention, the intermediates of formula (II) and (III) are used for the preparation of Ivacaftor.

According to embodiments of the present invention, the methods are in particular be more industrially scalable, and allow the desired compounds to be obtained with high yields, and use cheaper reagents which are simpler to handle and more industrial applicable.

The process details of the invention are provided in the examples given below, which are provided by way of illustration only and therefore should not be construed to limit the scope of the invention.

EXPERIMENTAL PROCEDURE

Example-1

Stage-I: Preparation of 2, 4 di-tert-butyl phenyl ethyl carbonate

A clean and dry 5 liter round bottom flask, fitted with mechanical stirrer, thermopocket and dropping funnel was charged with Dichloromethane (2000 ml), 2,5 Di-tertiary butyl phenol (500 g) and Dimethyl amino pyridine (15 g) at room temperature. The reaction mass was cooled to 15-20° C. and Triethyl amine (470 g) was slowly added over 50-70 minutes at 15-20° C. The reaction mass was cooled to 0-5° C., and Ethyl chloroformate (393 g) was slowly added over 60-90 minutes while maintaining the internal temperature at 0-5° C. The temperature was raised to 20-25° C. and maintained under stirring for 40-60 minutes at 20-25° C. and progress of reaction was monitored by TLC (unreacted starting material phenol was below 1.0%). After completion of the reaction, water (1000 ml) was added to reaction mass and maintained under stirring for 10-20 minutes at 20-25° C. to get clear solution. The layers were separated and the aqueous layer was extracted with Dichloromethane (1000 ml). Both the organic layers were combined and washed with water (1000 ml). The organic layer was dried with sodium sulphate and the solvent Dichloromethane was distilled out completely under vacuum to remove traces of solvent to obtain the title compound (630-660 grams) as light yellow colored viscous oil.

Example-2

Preparation of 2, 4 di-tert-butyl-5-nitro phenyl ethyl carbonate

A clean and dry 5 liter round bottom flask, fitted with mechanical stirrer, thermopocket and dropping funnel was charged with Sulfuric acid (1250 ml) and cooled to 0-5° C. 2, 5 Di-tertiary butyl phenyl ethyl carbonate (500 g) obtained in example-1 was slowly added. The resultant composition was maintained under stirring for 10 minutes and Potassium Nitrate (143.35 g) was added portion-wise over 40-60 minutes while maintaining the internal temperature at 0-10° C. After completion of the reaction, water (2500 ml) was slowly added at below 30° C.; followed by addition of ethyl acetate (2500 ml) and the resultant mixture was maintained under stirring for 20 minutes. The organic layer was separated and the aqueous layer was extracted with ethyl acetate (2×1250 ml). All organic layers were combined and washed with water (2500 ml). The ethyl acetate was distilled out under reduced pressure to obtain an oily residue which contained a mixture of 2, 4 di-tert-butyl-5-nitro phenyl ethyl carbonate and 2, 4 di-tert-butyl-6-nitro phenyl ethyl carbonate.

Example-3

Preparation of 2, 4 di-tert-butyl-5-nitro phenol

A clean and dry 5 liter round bottom flask, fitted with mechanical stirrer, thermo pocket and dropping funnel was charged with Methanol (2500 ml) and the mixture of 2, 4 di-tert-butyl-5-nitro phenyl ethyl carbonate and 2, 4 di-tert-butyl-6-nitro phenyl ethyl carbonate (obtained in example-2) at 25-30° C. The reaction mass was cooled to 0-5° C. and Potassium hydroxide (260 g) was added portion-wise while maintaining the internal temperature 0-5° C. The temperature was raised to 25-30° C. and maintained under stirring for 60-90 minutes for completion of the reaction. After completion of the reaction, the reaction mass was cooled to 10-15° C. and the pH was adjusted to 2-3 with dilute hydrochloric acid (~800 ml). The flask was then charged with water (2500 ml) and ethyl acetate (2500 ml) and stirred for 15-20 minutes at 25-30° C. The organic layer was separated and the aqueous layer was extracted with ethyl acetate (2×1250 ml). All organic layers were combined and washed with water (2500 ml). The ethyl acetate was distilled out under reduced pressure at 45-50° C. to obtain an oily residue. Charged n-hexane (250 ml) and distilled out n-hexane completely to remove traces of ethyl acetate. The reaction mass was cooled to 0-5° C. and maintained under stirring for 90-120 minutes at 0-5° C. The resultant composition was filtered and washed with chilled n-hexane (100 ml). The wet product was dried at 45° C. to obtain title compound 130-170 grams.

Example-4

Preparation of 2, 4 di-tert-butyl-5-aminophenol

Method-A:

2, 4 di-tert-butyl-5-nitro phenol (100 g) was dissolved in isopropyl alcohol (400 ml) at room temperature and charged to an autoclave vessel. Charge 20 grams Raney Nickel (Previously washed with water and dried with isopropyl alcohol). The vessel was fitted on an autoclave and flushed with hydrogen gas two times. The reaction mass maintained under hydrogen gas pressure (4-6 kg) at room temperature for 90-240 minutes. The progress of reaction mass was monitored by TLC (The starting material nitro compound was below 0.5%). After completion of the reaction, the Raney nickel catalyst was separated by filtration and the hyflo bed was washed with isopropyl alcohol (100 ml). The filtrate was charged to the RB flask and water (1000 ml) was added drop wise in 60-90 minutes at 20-25° C. The slurry was maintained under stirring for 60-90 minutes at same temperature. The crude product was collected by filtration and washed with water (100-200 ml). The wet solid obtained was dried in air oven for 4 hours at 45-50° C. The semidry solid was taken in Toluene (200 ml) and the reaction mass was heated to 70-80° C.; maintained at 70-80° C. for 60 minutes and then cooled to 0-5° C. The slurry was stirred at 0-5° C. for 60-90 minutes. The resultant solid was filtered, washed with chilled toluene (50 ml) and dried at 45-50° C. for 6-8 hours to obtain the title compound (55-70 grams) as light pink colored crystalline solid.

Method-B:

2, 4 di-tert-butyl-5-nitro phenol (100 g) was dissolved in isopropyl alcohol (400 ml) at room temperature and charged to an autoclave vessel. Charged 3-4 ml of methane sulfonic acid to adjust the pH to 3-4 and followed by 2.0 grams Palladiun carbon (5%, 50% wet). The vessel was fitted on an autoclave and flushed with hydrogen gas two times. The reaction mass was maintained under hydrogen gas pressure (4-6 kg) at room temperature for 90-240 minutes. After completion of the reaction, the catalyst was separated by filtration and the hyflo bed was washed with isopropyl alcohol (100 ml). The filtrate was charged to the RB flask and water (1000 ml) was added drop wise in 60-90 minutes at 20-25° C. The slurry was maintained under stirring for 60-90 minutes at the same temperature. The crude product was collected by filtration and washed with water (100-200 ml). The obtained wet solid was dried in air oven for 4 hours at 45-50° C. The semidry solid was taken in Toluene (200 ml) and the reaction mass heated to 70-80° C., stirred for 60 minutes at the same temperature and cooled to 0-5° C. The resultant solid was filtered, washed with chilled toluene (50 ml) and dried at 45-50° C. for 6-8 hours to obtain the title compound (55-70 grams) as light pink colored crystalline solid.

Example-5

Preparation of 4-Oxo 1, 4-dihydroquinoline-3-carboxylic add

Step a): 2-Phenylaminomethylene malonic acid diethyl ester

A mixture of aniline (100 g) and Diethyl-2-(ethoxymethylene) malonate (232 g) was heated to 140-150° C. for 2-3 hours. After completion of reaction, the mixture was cooled to 50-55° C. and dried under reduced pressure for 3 hours to obtain 2-Phenylaminomethylene malonic acid diethyl ester as yellow colored solid, which was used in the next step of preparation without purification.

Step b): 4-hydroxyquinoline 3-carboxylic acid ethyl ester

A clean and dry 1 liter round bottom flask, fitted with mechanical stirrer and thermo pocket was charged 2-Phenylaminomethylene malonic acid diethyl ester (100 g) and Eaton's reagent (400 ml) at room temperature. The reaction mass was heated to 80-90° C. and maintained under stirring for 4-6 hours at the same temperature. After completion, the reaction mass was cooled to 5-10° C. and was treated with aqueous sodium carbonate solution at 0-10° C. and stirred for 60-90 minutes at the same temperature. The resultant solid was filtered, washed with water (until the water filtrate showed neutral pH) and dried at 45-50° for 6-8 hours to obtain 4-hydroxyquinoline 3-carboxylic acid ethyl ester (70-80 g)

Step c): 4-Oxo 1,4-dihydroquinoline-3-carboxylic acid 4-hydroxyquinoline 3-carboxylic acid ethyl ester (100 g) was suspended in 2N sodium hydroxide solution at room temperature and was heated to 90-100° C. and maintained for 2-4 hours. After completion, the reaction mass was cooled to room temperature and filtered to remove undissolved material. The obtained filtrate was acidified to pH 3-4 with 2N Hydrochloric acid at 25-30° C. The resultant solid was filtered, washed with water and dried at 50° C. until constant weight was observed to obtain the title compound (55-65 g).

Example: 6

Preparation of 5-amino-2, 4-di-tert-butylphenyl methyl carbonate

To a solution of 2, 4 di-tert-butyl-5-aminophenol (10 g) in diethyl ether (100 ml) and triethylamine (10.1 ml), was added methyl chloroformate (7.46 ml) dropwise at 0° C. The mixture was then allowed to warm to room temperature and was stirred for 6 to 8 hours. The reaction was then filtered, and the filtrate was cooled to 0° C., and an additional 5 mL triethylamine and 3.7 mL methyl chloroformate was then added and the reaction was allowed to warm to room temperature and then stirred for an addition 1 hours. At this stage, the reaction was almost complete and was worked up by filtering, then washing with water, followed by brine. The solution was then concentrated under vacuum to obtain the title compound Example: 7

Preparation of N-(2, 4-di-tert-butyl-5-hydroxyphenyl)-4-oxo-1,4-dihydroquinoline-3-carbox-amide (Ivacaftor)

To a solution of 4-Oxo-1,4-dihydroquinoline-3-carboxylic acid (1.0 eq) in 2-Me THF added 5-amino-2,4-di-tert-, butylphenyl methyl carbonate (1.1 eq), Propane phosphonic acid anhydride 50% solution in 2-MeTHF (1.7 eq) was added, followed by Pyridine (2.0 eq) and the resultant suspension was heated to 45° to 50° C., and held at this same temperature for 8 to 10 hours, until completion of the reaction (checked for completion by HPLC). Once complete, the resulting mixture was cooled to 20-25° C., and 2-MeTHF (12.5 vol) was added to dilute the mixture. The reaction mixture was then washed with water (10.0 vol)., and 2-MeTHF was added to bring the total volume of the reaction to 40.0 vol. To this solution was added NaOMe/MeOH (1.7 equiv) followed by stirring for 1 to 2 hour, where the reaction was checked for completion by HPLC. Once complete, the reaction was quenched with 1 N HCl (10.0 vol), and washed with 0.1 N HCl (10.0 vol). The organic solution was filtered and the filtrate concentrated at 35° C. to obtain a residue. The residue was charged in 40:20 acetonitrile and water, the slurry was stirred for 5 to 6 hours and then cooled to 0° C. hours, followed by stirring for 2 hours. The resultant solid was filtered and dried under vacuum to obtain a title compound.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

The invention claimed is:
1. A method of preparing Ivacaftor, the method comprising:
(a) producing 4-Oxo-1,4-dihydro-quinoline-3-carboxylic acid of formula (II) by a process comprising the steps of:
(i) reacting aniline with diethyl-2-(ethoxymethylene) malonate;
(ii) treating the product of step a) with Eaton's reagent and heating to 80-90° C.;
(iii) cooling the product of step b) and neutralizing with an alkali carbonate;
(iv) hydrolyzing the product of step c) with an inorganic base; and
(v) isolating the intermediate of formula (II); and
(b) reacting the 4-Oxo-1,4-dihydro-quinoline-3-carboxylic acid of formula (II) with 2, 4 ditertiary butyl-5-amino-phenol of formula (III) in presence of O-Benzotriazole-N,N,N',N'-tetramethyl-uronium-hexafluorophosphate (HBTU) and triethyl amine to obtain the compound of Ivacaftor of formula (I) according to Scheme-I:

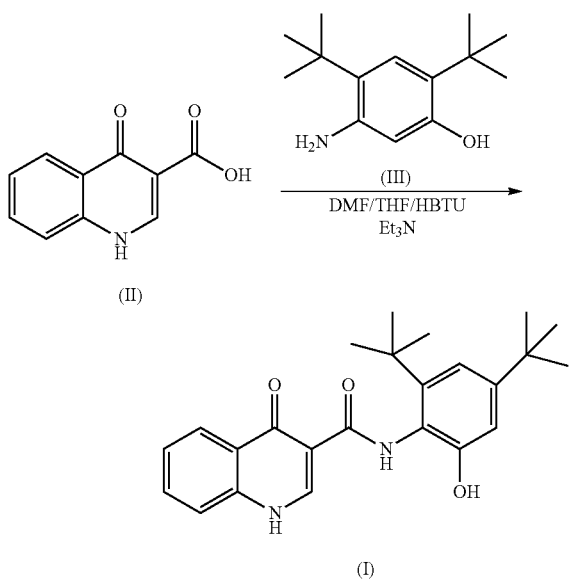

2. The method according to claim 1, wherein the reacting of aniline with diethyl-2-(ethoxymethylene) malonate occurs in absence of a solvent at a temperature ranging from 130-160° for 2-5 hrs.

3. The method according to claim 2, wherein the reacting of aniline with diethyl-2-(ethoxymethylene) malonate occurs at a temperature ranging from 140-150° C. for 2-3 hrs to obtain a compound of formula (V).

4. The method according to claim 1, wherein the compound of formula (V) is further treated with Eaton's reagent to get a cyclized compound of formula (IV).

5. The method according to claim 1, wherein the compound of formula (IV) is hydrolyzed in presence of the inorganic base to give a 4-Oxo-1, 4-dihydro-quinoline-3-carboxylic acid of formula (II).

6. The method according to claim 1, wherein the inorganic base is selected from sodium hydroxide, calcium hydroxide and potassium hydroxide.

7. The method according to claim 1, wherein the method comprises producing the compound of formula (III) by the process comprising the steps of:

a) reacting 2,5 di-tertiary butyl phenol with an alkyl chloroformate in the presence of an organic base;
b) nitrating the product of step a) to obtain a mixture of 2, 4 di-tert-butyl-5-nitro phenyl carboxylic alkyl ester and 2,4 di-tert-butyl-6-nitro phenyl carboxylic alkyl ester;
c) separating the 2,4 di-tert-butyl-5-nitro phenyl carboxylic alkyl ester by crystallization with an aliphatic solvent;
d) hydrolyzing the product of step c);
e) reducing the product of step d) in presence of Raney/nickel; and
f) isolating the compound of formula (III).

8. The method according to claim 7, wherein the alkyl chloroformate is selected from ethyl chloroformate, methyl chloroformate (or) isopropyl chloroformate.

9. The method according to claim 7, wherein the organic base is selected from triethylamine, Dimethylaminopyridine (or) pyridine.

10. The method according to claim 7, wherein the nitrating comprises employing a nitrating agent selected from $KNO_3/H_2SO_4$, $NaNO_3/H_2SO_4$ (or) $HNO_3/H_2SO_4$.

11. The method according to claim 7, wherein the aliphatic solvent is selected from n-hexane, cyclohexane, isobutyl ether, Tetrahydrofuran (or) methyl tertiary butyl ether; aromatic solvent is selected from toluene, mesitylene (or) xylene.

12. The method according to claim 1, wherein the method comprising producing the compound of formula (III) by the process comprising the steps of:
a) reacting the 2,5 di-tertiary butyl phenol with an alkyl chloroformate in the presence of an organic base;
b) nitrating the product of step a);
c) hydrolyzing the product of step b) to obtain a mixture of 2, 4 di-tert-butyl-5-nitro phenol and 2, 4 di-tert-butyl-6-nitro phenol;
d) separating the 2, 4 di-tert-butyl-5-nitro phenol by crystallization with an aliphatic solvent;
e) reducing the product of step d) in presence of Raney/nickel; and
f) isolating the compound of formula (III).

13. The method according to claim 12, wherein the alkyl chloroformate is selected from ethyl chloroformate, methyl chloroformate (or) isopropyl chloroformate.

14. The method according to claim 12, wherein the organic base is selected from triethylamine, Dimethylaminopyridine (or) pyridine.

15. The method according to claim 12, wherein the nitrating comprises employing a nitrating agent selected from $KNO_3/H_2SO_4$, $NaNO_3/H_2SO_4$ (or) $HNO_3/H_2SO_4$.

16. The method according to claim 12, wherein the aliphatic solvent is selected from n-hexane, cyclohexane, isobutyl ether, Tetrahydrofuran (or) methyl tertiary butyl ether; aromatic solvent is selected from toluene, mesitylene (or) xylene.

17. The method according to claim 1, the method further comprising producing the compound of formula (II) by a process comprising the steps of:
a) reacting aniline with diethyl-2-(ethoxymethylene) malonate;
b) treating the product of step a) with Eaton's reagent and heating to 80-90° C.;
c) cooling the product of step b) and neutralizing with an alkali carbonate;
d) hydrolyzing the product of step c) with an inorganic base; and
e) isolating the intermediate of formula (II); and producing the compound of formula (III) by the process comprising the steps of:
a) reacting 2,5 di-tertiary butyl phenol with an alkyl chloroformate in the presence of an organic base;
b) nitrating the product of step a) to obtain a mixture of 2, 4 di-tert-butyl-5-nitro phenyl carboxylic alkyl ester and 2, 4 di-tert-butyl-6-nitro phenyl carboxylic alkyl ester;
c) separating the 2, 4 di-tert-butyl-5-nitro phenyl carboxylic alkyl ester by crystallization with an aliphatic solvent;
d) hydrolyzing the product of step c);
e) reducing the product of step d) in presence of Raney/nickel; and
f) isolating the compound of formula (III).

18. The method according to claim 1, the method further comprising producing the compound of formula (II) by a process comprising the steps of:
a) reacting aniline with diethyl-2-(ethoxymethylene) malonate;
b) treating the product of step a) with Eaton's reagent and heating to 80-90° C.;
c) cooling the product of step b) and neutralizing with an alkali carbonate;
d) hydrolyzing the product of step c) with an inorganic base; and
e) isolating the intermediate of formula (II); and producing the compound of formula (III) by the process comprising the steps of:
a) reacting the 2,5 di-tertiary butyl phenol with an alkyl chloroformate in the presence of an organic base;
b) nitrating the product of step a);
c) hydrolyzing the product of step b) to obtain a mixture of 2, 4 di-tert-butyl-5-nitro phenol and 2, 4 di-tert-butyl-6-nitro phenol;
d) separating the 2, 4 di-tert-butyl-5-nitro phenol by crystallization with an aliphatic solvent;
e) reducing the product of step d) in presence of Raney/nickel; and
isolating the compound of formula (III).

19. The method according to claim 1, wherein the alkali carbonate is selected from the group consisting of sodium bicarbonate, potassium carbonate, sodium carbonate and calcium carbonate.

* * * * *